United States Patent

Mihailovski

[11] 3,933,468
[45] Jan. 20, 1976

[54] HERBICIDAL COMPOSITIONS

[75] Inventor: Alexander Mihailovski, Berkeley, Calif.

[73] Assignee: Stauffer Chemical Company, Westport, Conn.

[22] Filed: Aug. 26, 1974

[21] Appl. No.: 500,217

Related U.S. Application Data

[62] Division of Ser. No. 247,671, April 26, 1972, Pat. No. 3,860,410, which is a division of Ser. No. 99,658, Dec. 18, 1970, abandoned.

[52] U.S. Cl. .................................................. 71/95
[51] Int. Cl.² ........................................... A01N 9/22
[58] Field of Search ....................... 71/95, 120, 99

[56] References Cited
UNITED STATES PATENTS 3,741,796  6/1973  Marrese et al. ..................... 71/99
3,806,537  4/1974  Dorschner et al. .................. 71/99

*Primary Examiner*—Glennon H. Hollrah
*Attorney, Agent, or Firm*—Daniel C. Block

[57] ABSTRACT

New compounds corresponding to the generic formula:

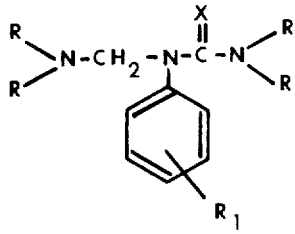

wherein X can be oxygen or sulfur, R can be lower alkyl or two R groups can form a ring structure, $R_1$ can be hydrogen, halogen, haloalkyl, alkyl or alkoxy.

6 Claims, No Drawings

HERBICIDAL COMPOSITIONS

This is a division, of application Ser. No. 247,671, filed Apr. 26, 1972, now U.S. Pat. No. 3,860,410, which is in turn a division of application Ser. No. 99,658, filed Dec. 18, 1970, now abandoned.

DESCRIPTION OF THE INVENTION

This invention is directed to a novel group of compounds which may be generally described as dialkylaminomethylene urea derivatives which are highly active herbicides. The compounds of the present invention are represented by the generic formula:

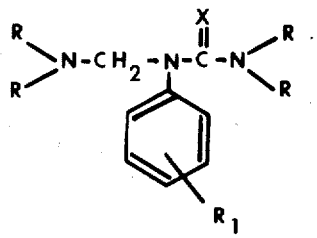

wherein X can be oxygen or sulfur, R can be lower alkyl or two R groups can form a ring structure, $R_1$ can be hydrogen, halogen, haloalkyl, alkyl or alkoxy.

The above-noted compounds can be prepared by combining a tetraalkyl diaminomethane with an aryl isocyanate in an inert solvent such as ethyl ether, benzene, methylene chloride or the like at room temperature or lower. The products form very rapidly and can be isolated in good purity upon evaporation of the solvent.

In order to illustrate the merits of the present invention the following examples are provided:

EXAMPLE 1

Preparation of 1-(dimethylaminomethylene)-1-(3'-trifluoromethylphenyl)-3,3-dimethylurea.

To 71.0 g. (0.695 moles) N,N,N',N'-tetramethyldiaminomethane in 200 ml. ethyl ether were added dropwise 130 g. (0.695 moles) metatrifluoromethylphenyl isocyanate dissolved in 150 ml. ethyl ether while cooling the reaction flask in an ice bath. The resulting clear solution was stirred at room temperature for a further three hours. The solvent was removed by evaporation to give 199 g. of liquid product. $n_D^{30}$ 1.4840.

EXAMPLE 2

Preparation of 1-(diethylaminomethylene)-1-(4'-chlorophenyl)-3,3-diethylurea.

To 7.0 g. (0.044 moles) N,N,N',N'-tetraethyldiaminomethane in 20 ml. ethyl ether were added slowly 6.8 g. (0.044 moles) 4-chlorophenyl isocyanate dissolved in 15 ml. ether. The reagents were stirred for 18 hours at room temperature and then the solvent was evaporated to give 13.5 g. of liquid product.

Other compounds were prepared in an analogous manner starting with the appropriate starting materials as outlined above. The following is a table of compounds representative of those embodied by the present invention. Compound numbers have been assigned to them and are used for identification throughout the balance of the specification.

TABLE I

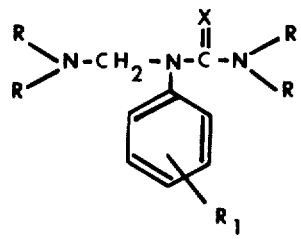

| Compound No. | X | R | $R_1$ |
| --- | --- | --- | --- |
| 1 | O | $CH_3$ | H |
| 2 | O | $CH_3$ | 4—Cl |
| 3 | O | $CH_3$ | 4—F |
| 4 | O | $CH_3$ | 3,4—Cl |
| 5 | O | $CH_3$ | 3—$CF_3$ |
| 6 | O | $CH_3$ | 3—$CF_3$, 4—Cl |
| 7 | O | $-(CH_2)_5-$ | 3,5—Cl |
| 8 | O | $-(CH_2)_5-$ | H |
| 9 | O | $-(CH_2)_5-$ | 3—$CF_3$ |
| 10 | O | $-(CH_2)_5-$ | 3—Cl |
| 11 | O | $-(CH_2)_5-$ | 4—Cl |
| 12 | O | $CH_3$ | 3—Cl |
| 13 | O | $CH_3$ | 4—Br |
| 14 | O | $CH_3$ | 2—F |
| 15 | O | $CH_3$ | 2—$CH_3$ |
| 16 | O | $CH_3$ | 4—$OCH_3$ |
| 17 | S | $CH_3$ | H |
| 18 | S | $CH_3$ | 4—F |
| 19 | O | $CH_2CH_3$ | H |
| 20 | S | $CH_2CH_3$ | H |
| 21 | O | $CH_2CH_3$ | 3—$CF_3$ |
| 22 | O | $CH_2CH_3$ | 4—Cl |
| 23 | O | $CH_3$ | 3,5—Cl |
| 24 | O | $CH_2CH_3$ | 3,5—Cl |

HERBICIDAL SCREENING TESTS

As previously mentioned, the novel compounds herein described are phytotoxic compounds which are useful and valuable in controlling various plant species. Compounds of this invention are tested as herbicides in the following manner.

Pre-emergence herbicide test. On the day preceding treatment, seeds of seven different weed species are planted in individual rows using one species per row across the width of the flat. The seeds used are hairy crabgrass (Digitaria sanguinalis (L.) Scop.), yellow foxtail (Setaria glauca (L.) Beauv.), watergrass (Echinochloa crusgalli (L.) Beauv.), California red oat (Avena sativa (L.)), redroot pigweed (Amaranthus retroflexus (L.), Indian mustard (Brassica juncea (L.) Coss.) and curly dock (Rumex crispus (L.). Ample seeds are planted to give about 20 to 50 seedlings per row, after emergence, depending on the size of the plants. The flats are watered after planting. The spraying solution is prepared by dissolving 50 mg. of the test compound in 3 ml. of a solvent, such as acetone, containing 1% Tween 20 (polyoxyethylene sorbitan monolaurate). The following day each flat is sprayed at the rate of 20 pounds of the candidate compound per 80 gallons of solution per acre. An atomizer is used to spray the solution on soil surface. The flats are placed in a greenhouse at 80°F. and watered regularly. Two weeks later, the degree of weed control is determined by comparing the amount of germination and growth of each weed in the treated flats with weeds in several untreated control flats. The rating system is as follows:
- − = no significant injury (0–15 percent control)
- + = slight injury (25–35 percent control)
- ++ = moderate injury (55–65 percent control)
- +++ = severe injury or death (85–100 percent control)

An activity index is used to represent the total activity on all seven weed species. It is the sum of the number of plus marks, so that an activity index of 21 represents complete control of all seven weeds. The results of this test are reported in Table II.

Post-emergence herbicide test. Seeds of five weed species including hairy crabgrass, watergrass, wild oats, Indian mustard, and curly dock and one crop pinto beans (*Phaseolus vulgaris*), are planted in flats as described above for pre-emergence screening. The flats are placed in the greenhouse at 72°–85°F. and watered daily with a sprinkler. About 10 to 14 days after planting when the primary leaves of the bean plant are almost fully expanded and the first trifoliate leaves are just starting to form, the plants are sprayed. The spray is prepared by weighing out 50 mg. of the test compound, dissolving it in 5 ml. of acetone containing 1 percent Tween 20 (polyoxyethylene sorbitan monolaurate) and then adding 5 ml. of water. The solution is sprayed on the foliage using an atomizer. The spray concentration is 0.5% and the rate would be approximately 20 lb./acre if all of the spray were retained on the plant and the soil, but some spray is lost so it is estimated that the application rate is approximately 12.5 lb./acre.

Beans are used to detect defoliants and plant growth regulators. The beans are trimmed to two or three plants per flat by cutting off the excess weaker plants several days before treatment. The treated plants are placed back in the greenhouse and care is taken to avoid sprinkling the treated foliage with water for 3 days after treatment. Water is applied to the soil by means of a slow stream from a watering hose taking care not to wet the foliage.

TABLE II

| Compound No. | SCREENING RESULTS | |
|---|---|---|
| | Pre-emergence | Post-emergence |
| 1 | 21 | 18 |
| 2 | 21 | 18 |
| 3 | 21 | 18 |

TABLE II-continued

| Compound No. | SCREENING RESULTS | |
|---|---|---|
| | Pre-emergence | Post-emergence |
| 4 | 21 | 18 |
| 5 | 21 | 18 |
| 6 | 21 | 18 |
| 7 | 3 | 11 |
| 8 | 19 | 18 |
| 9 | 18 | 16 |
| 10 | 18 | 17 |
| 11 | 18 | 17 |
| 12 | 19 | 18 |
| 13 | 19 | 18 |
| 14 | 18 | 17 |
| 15 | 20 | 18 |
| 16 | 14 | 18 |
| 17 | 17 | 16 |
| 18 | 19 | 17 |
| 19 | 20 | 18 |
| 20 | 13 | 12 |
| 21 | 20 | 18 |
| 22 | 20 | 18 |
| 23 | 19 | 17 |
| 24 | 13 | 14 |

What is claimed is:

1. The method of controlling undesirable vegetation comprising applying to the locus where control is desired an herbicidally effective amount of a compound having the generic formula

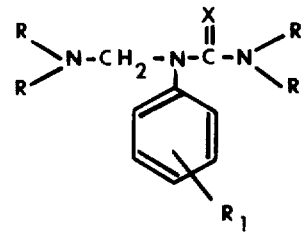

wherein X is oxygen or sulfur, each set of the two R groups form a ring structure having 4 carbon atoms, $R_1$ is hydrogen, halogen, haloalkyl, alkyl or alkoxy.

2. The method as set forth in claim 1 wherein X is O and $R_1$ is 3,5-Cl.

3. The method as set forth in claim 1 wherein X is O and $R_1$ is H.

4. The method as set forth in claim 1 wherein X is O and $R_1$ is 3-$CF_3$.

5. The method as set forth in claim 1 wherein X is O and $R_1$ is 3-Cl.

6. The method as set forth in claim 1 wherein X is O and $R_1$ is 4-Cl.

* * * * *